(12) United States Patent
Saukkonen et al.

(10) Patent No.: US 11,118,149 B2
(45) Date of Patent: Sep. 14, 2021

(54) BIOREACTOR BAGS

(71) Applicant: Global Life Sciences Solutions USA LLC, Marlborough, MA (US)

(72) Inventors: Hanna-Leena Saukkonen, Marlborough, MA (US); Ralph Stankowski, Westborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 111 days.

(21) Appl. No.: 16/394,601

(22) Filed: Apr. 25, 2019

(65) Prior Publication Data

US 2019/0330580 A1    Oct. 31, 2019

Related U.S. Application Data

(60) Provisional application No. 62/662,301, filed on Apr. 25, 2018.

(51) Int. Cl.
*C12M 1/00*    (2006.01)
*B01F 11/00*    (2006.01)
*C12M 3/06*    (2006.01)

(52) U.S. Cl.
CPC ............ *C12M 23/14* (2013.01); *C12M 29/14* (2013.01); *B01F 11/0005* (2013.01); *C12M 23/28* (2013.01); *C12M 27/16* (2013.01)

(58) Field of Classification Search
CPC .... B01F 11/0005; C12M 23/14; C12M 23/28; C12M 23/34; C12M 23/46; C12M 27/16; C12M 29/14
See application file for complete search history.

(56) References Cited

U.S. PATENT DOCUMENTS

| | | | |
|---|---|---|---|
| 7,364,065 B2 * | 4/2008 | Willemsen ............. | B65D 5/746 220/345.1 |
| 8,186,881 B2 * | 5/2012 | Lyon .................. | B65D 33/2591 383/69 |
| 2002/0009803 A1 * | 1/2002 | Vajta ...................... | C12M 21/06 435/325 |
| 2009/0211059 A1 * | 8/2009 | Byron ................ | B65D 33/1666 24/30.5 R |
| 2013/0343676 A1 * | 12/2013 | Dais ..................... | B65D 33/007 383/33 |
| 2019/0211292 A1 * | 7/2019 | Beauchesne ........... | C12M 27/16 |

* cited by examiner

*Primary Examiner* — Donald R Spamer
*Assistant Examiner* — Lauren A. Ryan
(74) *Attorney, Agent, or Firm* — Eversheds Sutherland (US) LLP

(57) ABSTRACT

Bioreactor bags formed from sheet materials are disclosed. The bioreactor bags include an opening which is openable and recloseable in a fluid tight manner for providing an opening for insertion of solid materials into the bag.

19 Claims, 3 Drawing Sheets

BIOREACTOR BAGS

CROSS-REFERENCE TO RELATED APPLICATIONS

This application claims the benefit of U.S. Provisional Application No. 62/662,301, filed Apr. 25, 2018, which is incorporated herein by reference in its entirety.

TECHNICAL FIELD

The present disclosure relates to bioreactors constructed as bags or bag-like containers for fluids for cultivation of cells, and more particularly, to bag bioreactors for cultivation under agitation by rocking.

BACKGROUND

The bio-processing industry has traditionally used stainless steel systems and piping in manufacturing processes for fermentation and cell culture. These devices are designed to be steam sterilized and reused. Cleaning and sterilization are however costly labour-intensive operations. Moreover, the installed cost of these traditional systems with the requisite piping and utilities is often prohibitive. Furthermore, these systems are typically designed for a specific process, and cannot be easily reconfigured for new applications. These limitations have led to adoption of a new approach in recent years—that of using plastic, single-use disposable bags and tubing, to replace the usual stainless steel tanks.

In particular bioreactors, traditionally made of stainless steel, have been replaced in many applications by disposable bags which are rocked to provide the necessary aeration and mixing necessary for cell culture. These single-use bags are typically provided sterile and eliminate the costly and time-consuming steps of cleaning and sterilization. The bags are designed to maintain a sterile environment during operation thereby minimizing the risk of contamination. Commonly used bags are of the "pillow style," mainly because these can be manufactured at low cost by seaming together two flexible sheets of plastic. Three-dimensional bags have also been described, where further sheets may be used to create wall structures.

One of the successful disposable bioreactor systems uses a rocking table on to which a bioreactor bag is placed. The bioreactor bag is partially filled with liquid nutrient media and the desired cells. The table rocks the bag providing constant movement of the cells in the bag and also efficient gas exchange from the turbulent air-liquid surface. The bag, typically, has at least one gas supply tube for the introduction of air, carbon dioxide, nitrogen or oxygen, and at least one exhaust gas tube to allow for the removal of respired gases. Nutrients can be added through other tubes.

SUMMARY

The construction of conventional bags does not allow for the introduction of solid materials such as tissue samples or semi-rigid organ scaffold constructions. That problem is addressed herein.

In embodiments, a bioreactor bag is formed from sheet materials and defines a resealable fluid-tight opening into the bag configured to allow insertion of a solid material into the bag.

Bioreactor bags according to the disclosure allow for the introduction of substantially solid materials.

The disclosure extends to any combination of features disclosed herein, whether or not such a combination is mentioned explicitly herein. Further, where two or more features are mentioned in combination, it is intended that such features may be claimed separately without extending the scope of the invention.

BRIEF DESCRIPTION OF THE DRAWINGS

Embodiments according to the disclosure can be put into effect in numerous ways, illustrative embodiments of which are described below with reference to the drawings, wherein.

DETAILED DESCRIPTION

Figure 1:
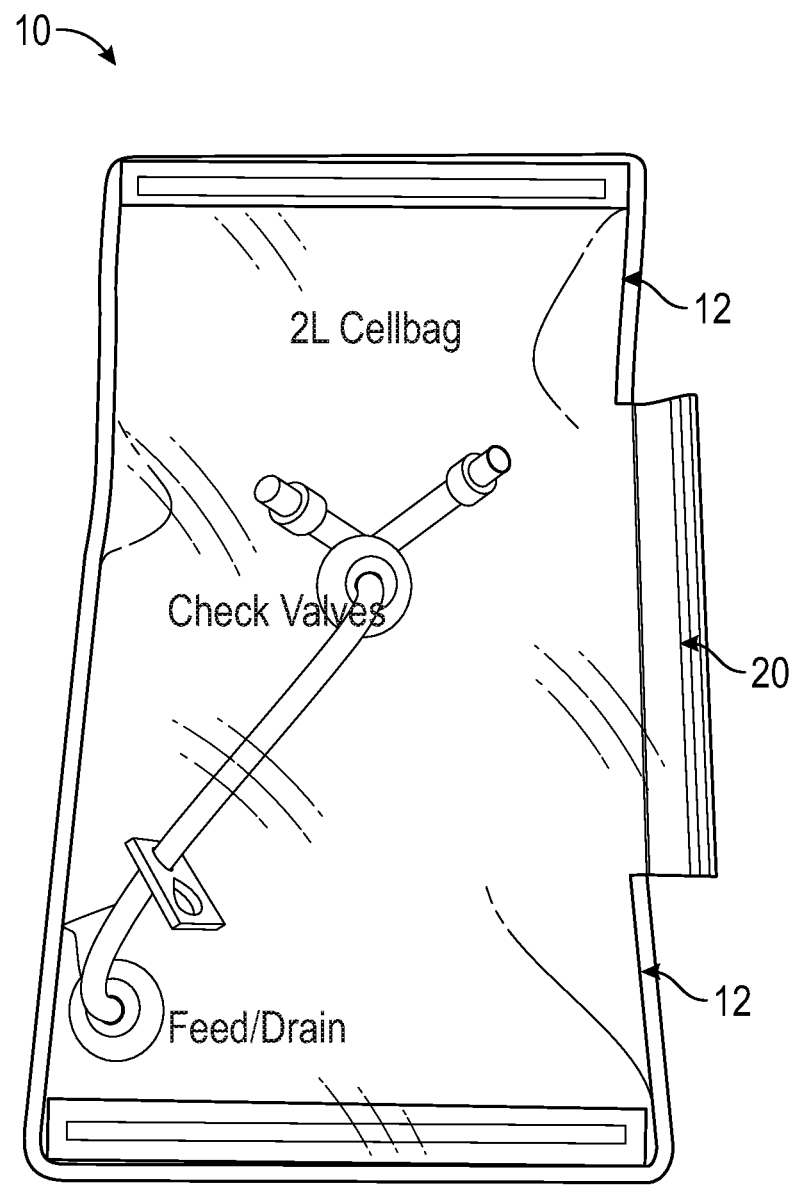
FIG. 1 shows a cell bag according to the invention.

The disclosure, together with its objects and the advantages thereof, may be understood better by reference to the following description taken in conjunction with the accompanying drawings, in which like reference numerals identify like elements in the drawings.

FIG. 1 shows a cell bag 10 formed from sheet materials. The bag includes a novel recloseable section 20 formed in a heat seal seam 12 of the bag 10. The recloseable section 20 provides a resealable fluid-tight opening into the bag configured to allow insertion of a solid material into the bag. Conventional valves and feed/drain port are illustrated also.

In some embodiments, the sheet materials include a polymeric material. In some embodiments, the polymeric material may be reinforced, for example, with reinforcing filaments, fabric, mesh, or other reinforcing structures in the sheet. The polymeric material may include single layer materials or multilayer materials, for example, multiextruded or laminated layers. The polymeric material may include a flexible polymer. The polymeric material may include one or more of polyethylene, for example, low density polyethylene (LDPE), linear low density polyethylene (LLDPE), polyester, nylon, polypropylene, polyurethane, metallized polymer, or any suitable polymer, blend, or composite. The material may be transparent, translucent, or opaque.

In some embodiments, the sheet materials include two sheets sealed together at a periphery of the bag 10. In some embodiments, the periphery of the bag 10 defines a polygon. The polygon may include any n-sided polygon, wherein n is greater than or equal to three. In some embodiments, the polygon is a rectangle or a square. In some embodiments, the opening is disposed at a side of the polygon. In some embodiments, the bag 10 defines a projecting lip including recloseable section 20 at the side of the polygon, the projecting lip defining the opening.

In some embodiments, the projecting lip includes a first panel and a second panel. The first panel includes a first portion, and the second panel includes a second portion resealable with the first portion. For example, the first panel and the second panel may define recloseable seal 24 formed from cooperating plastics formations which can be clipped together or pulled apart with force. Such seals are known and sold under the brand name of Ziploc® (S. C. Johnson, Racine, Wis.). In some examples, the seal 24 extends at least partly along a side of the bag 10. In some examples, the seal 24 extends along an entire length of a side of the bag 10.

In some embodiments, the first portion of the first panel defines a projecting rib extending along the lip, and the second portion of the second panel defines a receiving channel extending along the lip, with the projecting rib is configured to resealably engage with the receiving channel.

In some embodiments, the lip further comprises a sliding closure configured to slide along the projecting rib and receiving channel. The sliding closure includes a metal, alloy, or polymeric slider that slides along the lip to open or close the opening. The slider defines a channel and a tab configure to introduce the rib into the channel to seal them together when slid along a first direction and configured to extract and separate the rib from the channel when slid along the second direction.

In some embodiments, one or both of the first portion or the second portion comprise a fluid-tight resealable adhesive layer. The adhesive layer may include any suitable fluid-resistant resealable adhesive substantially impervious to fluids, for example, a waterproof pressure-sensitive adhesive. In some embodiments, the adhesive layer may be used in addition to, or instead of, the projecting rib and channel to seal the opening.

Figure 2:
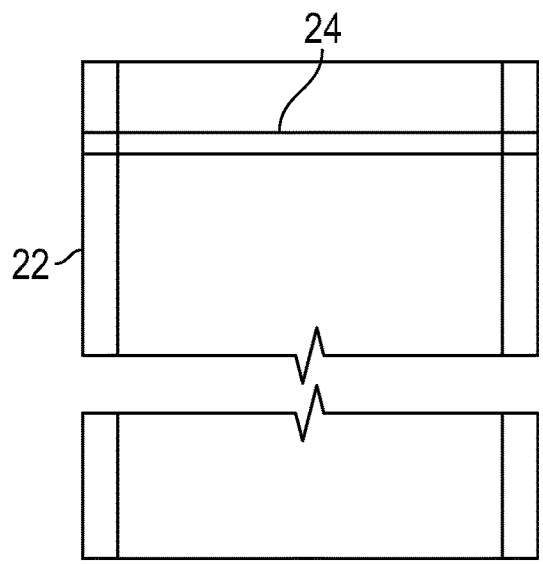
FIGS. 2, 3, 4, and 5 show constructional details of the bag of FIG. 1.
Figure 3:
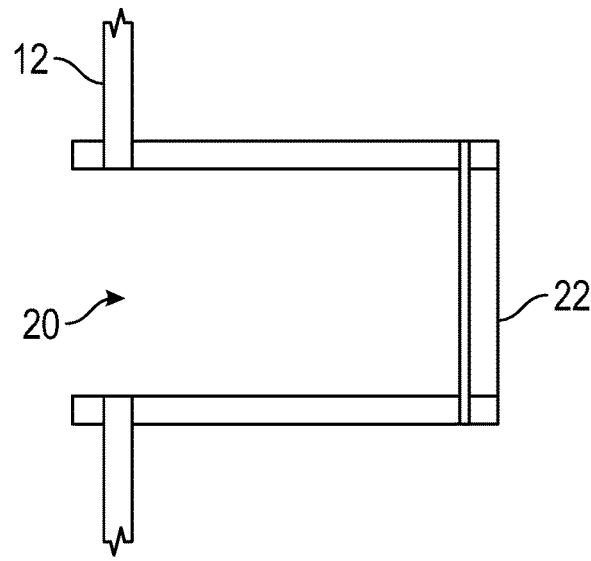
Figure 4:
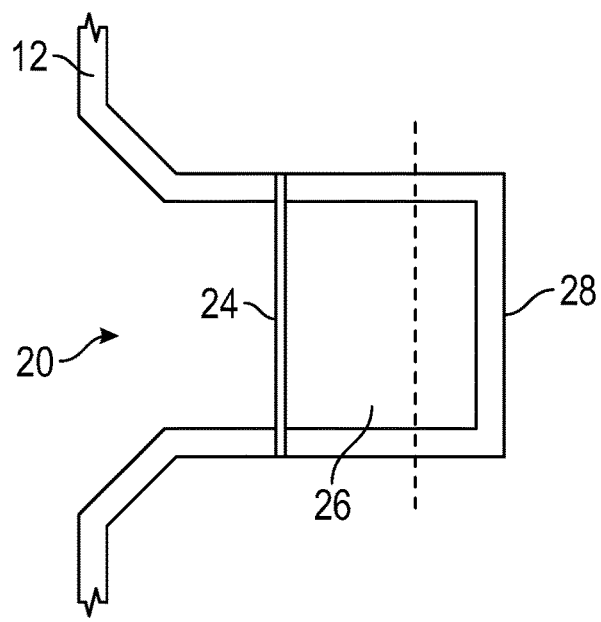

FIG. 2 shows a conventional plastics bag 22 which has been cut to provide a recloseable section of the cell bag 10 shown in FIG. 1. Top of the bag 22 has been heat-sealed into seam 12 and a section PTFE or the like as being inserted between the sheets of the bag 22 to prevent them from becoming sealed together. The resultant modified bag 10 provides the reclosable area 20, as shown in FIG. 3, for inserting or removing solid materials FIG. 4 shows a further modification to the bag 10 where the recloseable area 20 is extended beyond the recloseable seal 24, and includes an additional sealed area 26 which can be opened by the user if needed. The seal area 26 as a tear open heat seal 28.

Figure 5:
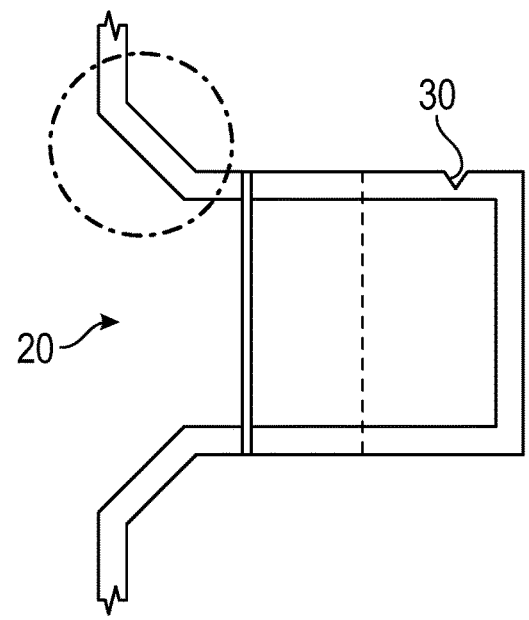

FIG. 5 shows a further modification to the recloseable area 20 where a notch 30 is used to aid the tearing of the seal area 26. Thus, the additional sealed area 26 and notch 30 may be used to maintain the opening closed until the point of first use, subsequent to which the opening may be resealed using recloseable area 20.

Figure 6:
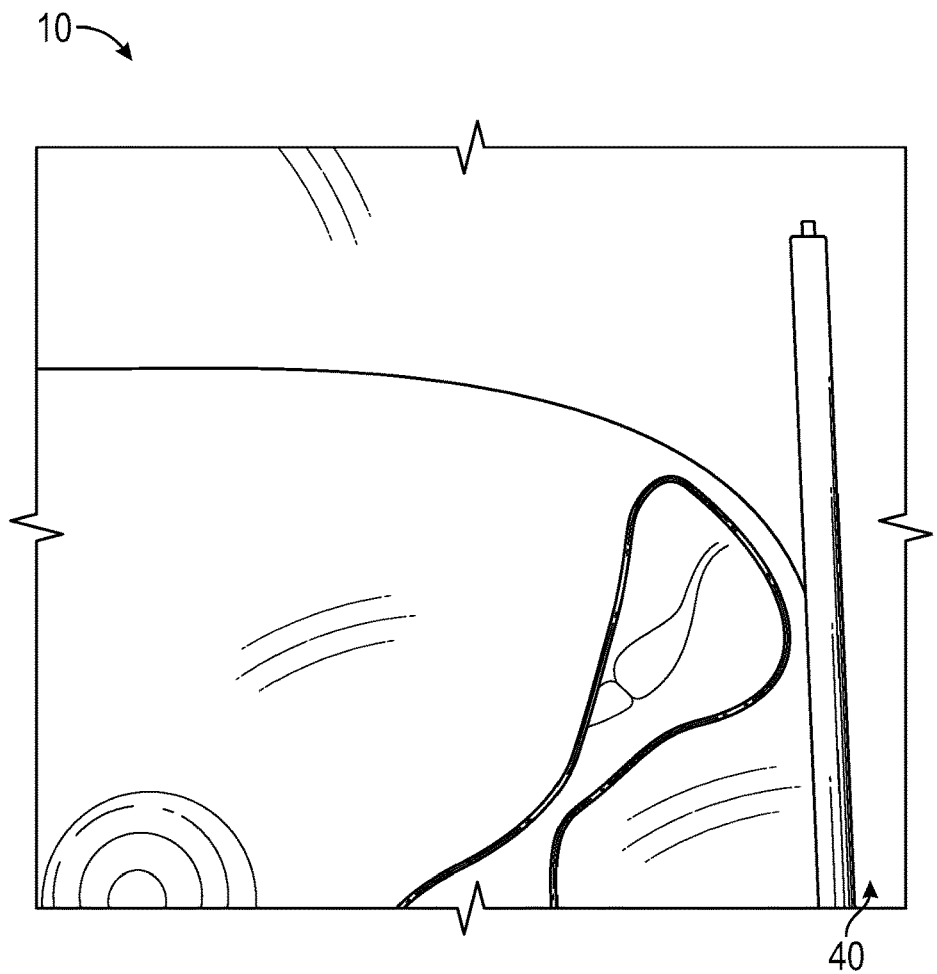
FIGS. 6 and 7 show a mechanical clamp feature for use with the bag of FIG. 1.
Figure 7:
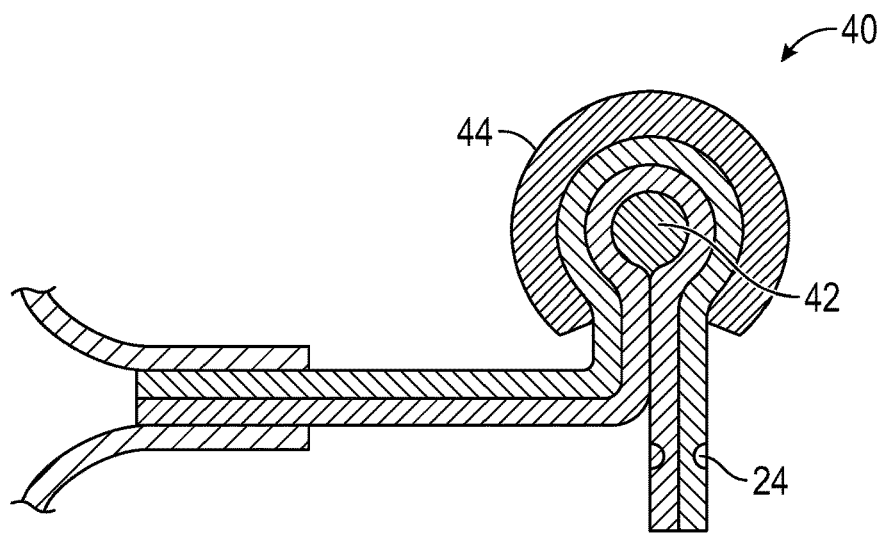

In use, where high-value experimentation is undertaken, there is a small risk that the recloseable seal 24 could fail by coming apart. To negate such a risk a mechanical clamp can be used to supplement the seal 24. FIGS. 6 and 7 show a mechanical clamp 40, in the form of an inner rod 42 around which is wrapped the recloseable area 20. A further C-shaped clamp 44 is clamped around that wrapped rod 42. In some embodiments, clamp 40 may be configured to further secure the bag to a wave rocker or another component, for example, instead of a cellbag rod. This arrangement provides a mechanical restriction which prevents the recloseable seal 24 from being exposed to significant fluid pressure. In some embodiments, one or both of inner rod 42 or C-shaped clamp 44 may include one or more of a metal, an alloy, a polymer, or a composite.

Although certain embodiments have been described and illustrated, it will be apparent to the skilled addressee that additions, omissions and modifications are possible to those embodiments without departing from the scope of the invention claimed.

The invention claimed is:

1. A bioreactor bag formed from sheet materials,
wherein the sheet materials define a heat-sealed seam at a periphery of the bioreactor bag,
wherein the bioreactor bag defines a projecting lip comprising a recloseable section defining a resealable fluid-tight opening at the periphery of the bag into the bag configured to allow insertion of a solid material into the bag,
wherein the seam extends in opposing directions from opposing ends of the recloseable section along the periphery of the bag on a same side of the bag as the recloseable section,
wherein the projecting lip comprises a first panel and a second panel, wherein the first panel comprises a first portion, and wherein the second panel comprises a second portion resealable with the first portion, and
wherein the lip extends in a direction transverse to the seam.

2. The bioreactor bag of claim 1, wherein the sheet materials comprise two sheets sealed together to form the seam at the periphery of the bag.

3. The bioreactor bag of claim 2, wherein the periphery of the bag defines a polygon.

4. The bioreactor bag of claim 3, wherein the opening is disposed at a side of the polygon.

5. The bioreactor bag of claim 4, wherein the projecting lip defines the opening.

6. The bioreactor bag of claim 3, wherein the polygon is a rectangle.

7. The bioreactor bag of claim 1, wherein the first portion of the first panel defines a projecting rib extending along the lip, and wherein the second portion of the second panel defines a receiving channel extending along the lip, wherein the projecting rib is configured to resealably engage with the receiving channel.

8. The bioreactor bag of claim 7, wherein the lip further comprises a sliding closure configured to slide along the projecting rib and receiving channel.

9. The bioreactor bag of claim 6, wherein one or both of the first portion or the second portion comprises a fluid-tight resealable adhesive layer.

10. The bioreactor bag of claim 7, wherein one or both of the first portion or the second portion comprises a fluid-tight resealable adhesive layer.

11. The bioreactor bag of claim 1, wherein the sheet materials comprise a flexible polymer.

12. The bioreactor bag of claim 1, further comprising a clamp extending along the opening, and covering the opening.

13. The bioreactor bag of claim 12, wherein the clamp defines a C-shaped transverse cross-section.

14. The bioreactor bag of claim 12, further comprising an inner rod extending along an interior of the clamp, wherein the clamp and the inner rod mechanically restrict the opening.

15. The bioreactor bag of claim 14, wherein the sheet materials adjacent the opening are secured between the clamp and the inner rod.

16. The bioreactor bag of claim 1, further comprising a valve fluidically coupled to an interior of the bag.

17. The bioreactor bag of claim 1, further comprising a feed/drain port fluidically coupled to an interior of the bag.

18. The bioreactor bag of claim 1, further comprising a filter assembly fluidically coupled to an interior of the bag.

19. The bioreactor bag of claim 1, further comprising a sample line fluidically coupled to an interior of the bag.

* * * * *